United States Patent [19]

Limb

[11] Patent Number: 4,832,842
[45] Date of Patent: May 23, 1989

[54] FILTER CHEST FOR USE WITH MULTIPLE FILTER UNITS, FOR LABORATORIES, AND WITH THE FILTER UNITS

[76] Inventor: Glenn R. Limb, 850 West Margate, Apt. 205, Chicago, Ill. 60640

[21] Appl. No.: 138,131

[22] Filed: Dec. 28, 1987

[51] Int. Cl.[4] ............................................. B01D 23/28
[52] U.S. Cl. .............................. 210/249; 210/323.2; 210/475; 210/476; 210/477; D24/32; 206/489; 206/562; 422/101
[58] Field of Search ................ 422/99, 101, 102, 104; 210/248, 249, 323.2, 341, 406, 416.1, 438, 445, 446, 450, 473, 474, 475, 476, 477, 497.01, 497.2; D24/31, 32; 206/139, 305, 372, 443, 446, 485, 488, 489, 569, 557, 560, 562

[56] References Cited

U.S. PATENT DOCUMENTS

| | | | |
|---|---|---|---|
| 3,319,792 | 5/1967 | Leder et al. | 210/406 |
| 3,956,125 | 5/1976 | Strutt et al. | 210/406 |
| 3,963,615 | 6/1976 | Plakas | 210/406 |
| 4,003,713 | 1/1977 | Bowser | 422/101 |
| 4,301,118 | 11/1981 | Eddlenan et al. | 422/101 |
| 4,642,220 | 2/1987 | Bjärknar | 422/101 |

Primary Examiner—Richard V. Fisher
Assistant Examiner—Wanda L. Millard
Attorney, Agent, or Firm—Paul H. Gallagher

[57] ABSTRACT

A chest in which a vacuum is formed. A removable tray in the form of a flat thin panel rests in the chest adjacent the top, and is provided with a pattern of holes in which test tubes are placed and supported. A cover has a similar pattern of holes in which filter units, containing samples to be tested, are placed in register with the test tubes respectively. The holes in the cover are provided with removable bosses for receiving and supporting the filter units, and sealing them. Stoppers are provided for sealing the holes in the cover when the filter units are not in place in the holes.

9 Claims, 2 Drawing Sheets

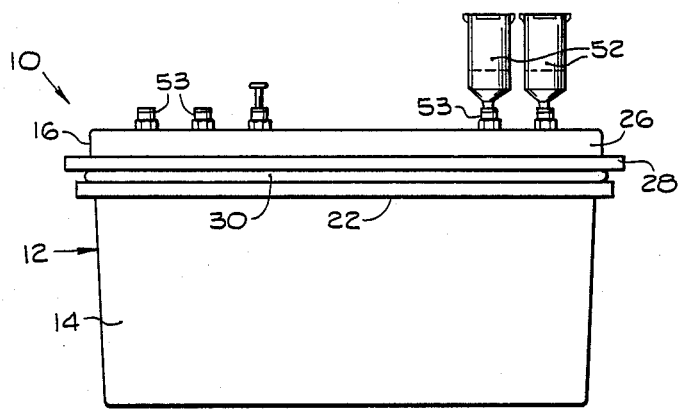
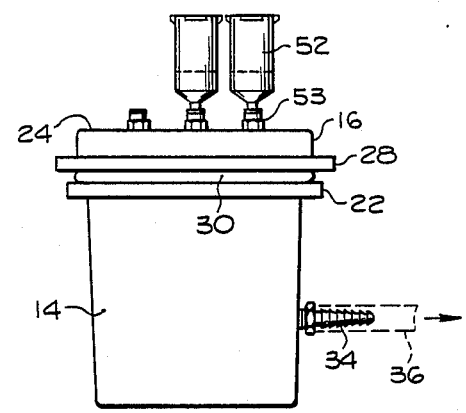
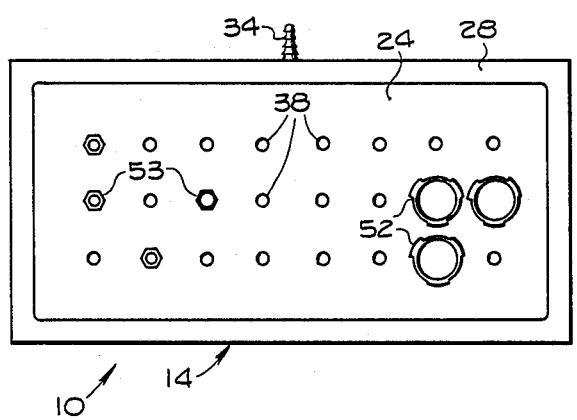
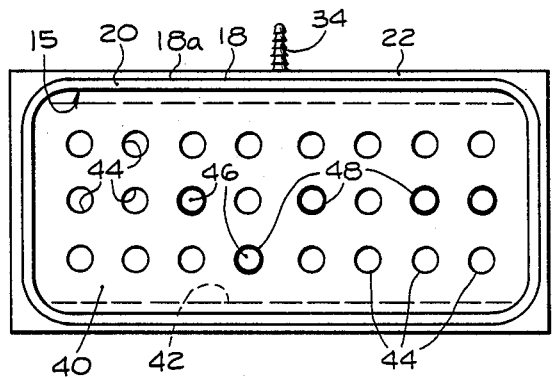
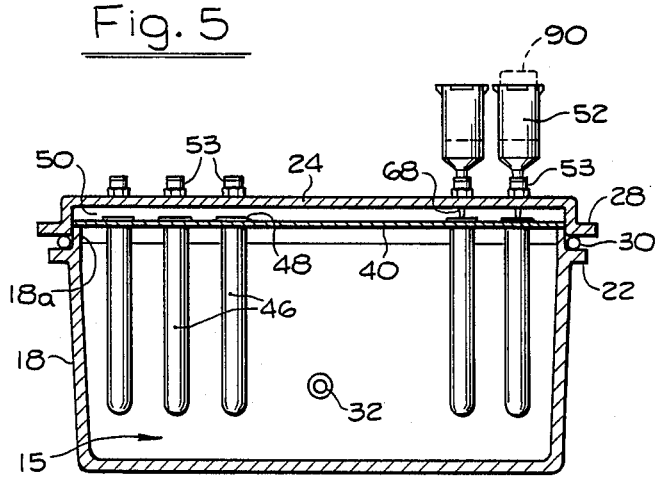
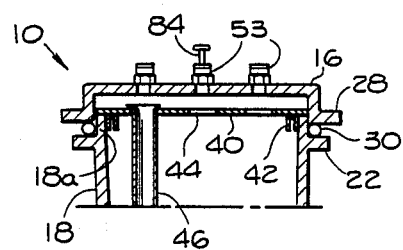

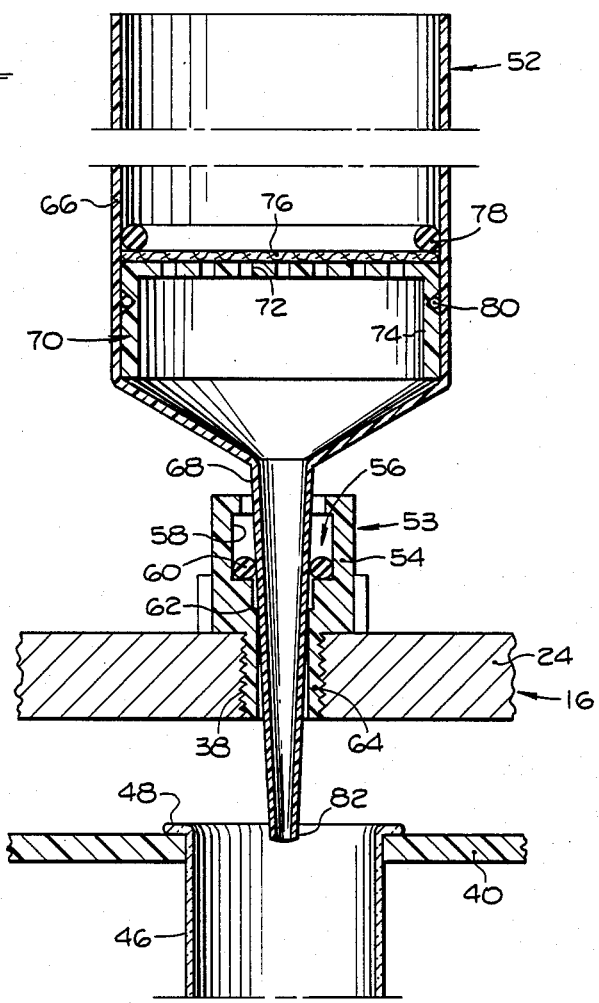
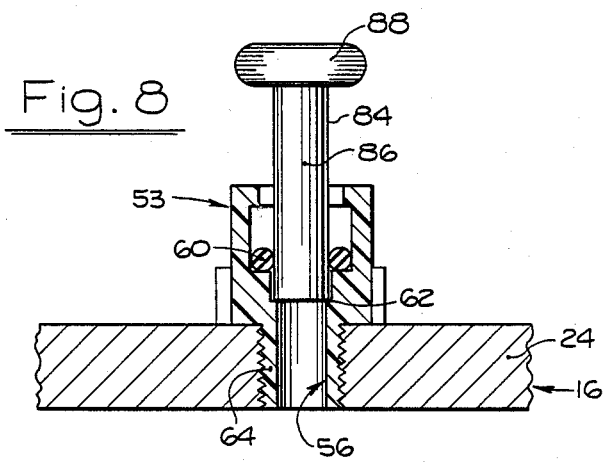

FILTER CHEST FOR USE WITH MULTIPLE FILTER UNITS, FOR LABORATORIES, AND WITH THE FILTER UNITS

FIELD OF THE INVENTION

The device resides in the field of filters most commonly used in laboratories, where a specimen is to be tested. The specimen is placed in an individual filter unit, and the liquid is expelled from the specimen into a test tube. A plurality of such filter units are accommodated in a vacuum filter.

OBJECTS OF THE INVENTION

A main object of the invention is to provide a multiple filter adapted especially for laboratories, having the following features and advantages.

1. It will accommodate a great number of filter units simultaneously, and enable the user to put successive filter units in place without interrupting the testing steps on filter units previously put in place.

2. It is extremely simple in construction, facilitating putting the filter units in place as stated.

3. Its simplicity renders it easy to clean, and less expensive to manufacture.

DESCRIPTION OF A PREFERRED EMBODIMENT

In the drawings,

FIG. 1 is a side elevational view of the multiple filter of the invention.

FIG. 2 is an end view from the right of FIG. 1.

FIG. 3 is a top view.

FIG. 4 is a top view with the cover removed.

FIG. 5 is a vertical longitudinal sectional view.

FIG. 6 is a vertical transverse sectional view of the upper portion only of the filter.

FIG. 7 is a vertical axial sectional view of a filter unit in position in the chest of the filter, and the related elements of the chest itself.

FIG. 8 is an axial vertical sectional view of the boss shown in FIG. 7 and a stopper therein.

Referring in detail to the drawings, the multiple filter is indicated in its entirety at 10 and it includes a chest 12, a body or main portion 14 defining a chamber 15, and a cover 16. The chest 12, having an open top, is of box-shape, or other suitable shape, and the body has a surrounding wall 18 having an upper edge 20. The body has a surrounding external flange 22 adjacent the top of the body, leaving an upper extremity 18a (FIGS. 5, 6) of the wall.

The cover 16 includes a top element 24, a surrounding downturned flange 26, and a horizontal outturned flange 28 at the bottom of the flange 26. The cover fits over the upper wall portion 18a preferably without substantial play therebetween. A surrounding resilient gasket 30 is fitted on the flange 22 on the body, and the cover rests on the gasket, providing a tight seal therebetween, to accommodate the vacuum to be produced in the chest.

The body 14 of the chest has a port 32 for fitting a nozzle 34 for connection with an air line 36 connected with a vacuum pump for producing a vacuum in the chest.

The cover 16 is provided with a pattern of holes 38 to be referred to again hereinbelow. These holes may be of any suitable number, such as 24 in the present case.

The multiple filter device includes a tray 40 which preferably is in the form of a thin, flat panel, and is provided with cleats 42 secured thereto on its under surface, along the long side edges thereof, and spaced inwardly from those edges. The tray is positioned on the upper edge surface 20 of the wall element 18a, and the cleats 42 are positioned for engaging the inner surface of the upper wall element 18a for locating the tray in the desired position. The tray is preferably of the same dimensions as the outer surface of the wall of the chest and when the cover is fitted on the body, the downturned flange 26 also surrounds the tray.

The tray is provided with a pattern of holes 44 therein in alignment with the holes 38, respectively, in the cover.

The tray 40 supports a plurality of test tubes 46 of conventional kind, being tubular with beads 48 surrounding the upper open ends of the test tubes. The test tubes are fitted in the holes and the beads rest on the tray and the test tubes are thereby supported in the chest.

The dimensions and proportions of the various elements are such that when the tray with the test tubes therein is fitted in place and the cover put in place, the upper ends of the test tubes are spaced from the under surface of the cover a small distance, as indicated at 50. This spacing is preferably very small, so as to eliminate or minimize splashing from the test tubes (FIGS. 7, 8), but the space provides vacuum to have effect on the filter elements referred to hereinbelow.

The multiple filter or device 10 includes a plurality of filter units 52, and can accommodate as many as there are holes 38 in the cover and they are aligned with the test tubes.

To accommodate the filter units 52 in a sealed and well supported position, each of the holes 38 is provided with a tubular boss 53, having a body 54 with a hole 56 therethrough. The hole 56 is provided with a counterbore 58 adjacent its top for reception of a sealing O-ring 60 and below the counterbore is an annular shoulder 62. The tubular boss, at its bottom, is provided with a reduced diameter threaded stud 64 which screws into the threaded holes 38 in the cover. When the bosses are in place in the holes, the upper large portions engage the surface of the cover and the lower ends of the studs are flush with the inner surface of the cover.

The filter unit 52 includes a funnel or shell 66, preferably cylindrical, having an open top and having a tubular stem 68 at the bottom, the stem preferably being tapered downwardly.

Within the funnel 66 is a filtering component 70, including a perforated disc 72 with a surrounding downwardly extending collar 74 which engages the lower reduced part of the shell, for spacing the perforated disc upwardly therefrom. A filter cloth 76 is fitted over the perforated disc.

A sealing O-ring 78 is fitted over the filter cloth, and another O-ring 80 is fitted in an annular groove in the collar portion 74. Either one or both of the O-rings 78, 80, may be used to seal the space between the filtering component and the funnel, eliminating the requirement for precision shaping of the corresponding elements.

The stem 68 is fitted through the tubular boss and is sealed by the O-ring 60, and the stem, below the O-ring, may engage another part of the boss to stably support the filter unit in proper vertical position. The stem 68 may be of desired length to extend down into the test tube a substantial distance as indicated at 82 to prevent splashing of the liquids in the test tubes.

FIG. 8 shows a stopper 84 for use in stopping the holes in the cover in which no filter units are placed (see also FIG. 6). The stopper 84 includes shank 86 and a cap 88, and the shank is inserted into a tubular boss 53 and engages the annular shoulder 62. The O-ring 60 seals the shank and stoppers the hole.

In the use of the multiple filter of the invention, the filter units 52 are placed in position in the holes 38 in the cover of the chest and the specimens then poured into the funnels. The extra holes 38, in which no filter units are placed, are stoppered by the stoppers 84. Then the vacuum pump is turned on.

In the case of a large number of samples being filtered simultaneously, the liquid would be filtered off in some of the units more rapidly than in others, and when the liquid of a sample is completely removed, that filter unit may be quickly stoppered by a second or filter stopper or plug 90 (FIG. 5) fitted in the funnel. It may also be feasible to remove the empty filter unit and insert a stopper 84, and while this latter step is not as satisfactory, it is to be noted that the holes 38 in the cover are relatively small, and one, or a few, holes that may be uncovered for a moment may no seriously affect the condition of the vacuum in the chest. Hence the operation of handling a plurality of filter units may be considered continuous, insofar as the application of the vacuum thereto is concerned.

The gasket 30 (FIGS. 1 and 5), which may be referred to as an O-ring, is relatively soft and pliable, and a tubular hose is utilized in the present case. By bearing down on the cover when the vacuum pump is turned on, a tight seal is established between the cover and the body. No clamps are required to keep the cover in place when the vacuum is formed, and in fact the whole device can be lifted by merely grasping the cover and lifting it.

The multiple filter or device, is extremely simple; the body has an inner surface that is clear of obstructions, being interrupted only by the outlet for the nozzle 34; the tray 40 is a simple, smooth, thin panel, and the test tubes are held in place only by engagement of the beads thereof on the tray; the cover then fits on the body surrounding the tray, and the interior of the cover is substantially clear of obstruction being interrupted only by the holes in the cover, and the lower or inner edges of the tubular bosses 53 are substantially flush with the inner surface of the cover. Accordingly the device can be easily cleaned and maintained clean.

The simple structure results in a relatively low manufacturing cost, and efficient operation thereof in normal use.

I claim:

1. A multiple filter comprising,
   a chest including a body and a removable cover,
   the body having an open top and forming a chamber and including a nozzle for connection with a vacuum pump for producing a vacuum in the chamber,
   the body having an outer seating surface adjacent the open top thereof, extending around the body,
   the cover consisting essentially of a thin plate and, when on the body, resting on the seating surface,
   a tray removably resting on the top edge of the body, and thereby positioned close to but spaced from the cover, the tray being so dimensioned that the seating surface is positioned outwardly of the tray, and the cover covering the tray and so engaging the seating surface to the exclusion of the tray,
   the tray and cover having a pattern of aligned holes, the holes in the tray being substantially larger than the holes in the cover,
   the tray being adapted for receiving test tubes in the holes therein and thereby supporting them within the chamber, and
   the cover being adapted for releasably receiving, in each hole therein, a filter unit separate from the cover, with an element of the filter unit extending through the hole into the interior of the chest and thereby in vertical alignment with the respective test tube, the cover being operable for supporting the filter unit in inserted position.

2. A multiple filter according to claim 1 wherein,
   the tray is detached and separate from the body and cover and devoid of fastening thereto and held in place only to loose confinement by the cover,
   the body includes a surrounding sidewall and has no outer flange surrounding the body adjacent to but spaced from the top and forming said outer sealing surface,
   a continuous gasket surrounding the upper portion of the body and resting on the outer seating surface, and
   the cover includes a downwardly extending flange surrounding the upper portion of the body and resting on the gasket when the cover is on the body, and the flange substantially engages the edges of the tray and constitutes the means for holding the tray against displacement in edgewise direction.

3. A multiple filter according to claim 1 for use with test tubes having beads surrounding their open upper ends and wherein,
   the tray is constituted by a thin flat panel having cleats on its under side engageable with an inner surface of the body for locating the cover on the body, and it supports the test tubes by the beads of the test tubes engaging and resting on marginal edges of the holes, and when the tray is in place, upper ends of the test tubes are closely adjacent to but spaced from an inner main surface of the cover.

4. A multiple filter according to claim 3 and including,
   a plurality of filter units,
   each filter unit including a main upper body and a reduced stem extending downwardly therefrom, the filter units being placeable in the holes in the cover, and being of such size and proportions that when they are placed in the holes the stems extend downwardly at least to the top of the test tubes.

5. A multiple filter according to claim 4 wherein,
   the cover includes a tubular boss surrounding each hole, adapted to receive the stem of the respective filter unit, and being of substantial vertical extent so as to be operable to retain the filter unit in vertical position.

6. A multiple filter according to claim 5 and including,
   a plurality of first stoppers, each including a shank and a cap,
   the stoppers being adapted to have their shanks inserted into the tubular bosses, with their caps engaging the upper ends thereof, for closing the holes,
   each tubular boss having a sealing ring therein, the sealing O-ring being operable for sealing by engaging the stems of the filter units and the shanks of the stoppers, respectively.

7. A multiple filter according to claim 5 wherein, the cover includes a main thin flat panel in which the holes are formed, and that panel, other than having the holes, is unobstructed.

the holes being internally threaded, and the bosses have lower externally threaded studs placed into the holes, said upper portions enlarged relative to the studs, and the bosses being positioned, when in the holes, with the upper portions engaging the panel of the cover, and lower ends of the studs do not extend below the inner surface of the panel and are substantially flush therewith.

8. A multiple filter according to claim 1 and including, filter stoppers for detachably fitting in, and stoppering the filter units.

9. A multiple filter according to claim 4 wherein, each filter unit includes in the body thereof, as a filtering component, a perforated plate and a filter cloth thereover, and sealing rings sealing the periphery between the perforated plate/filter cloth and the wall of the body of the filter unit.

* * * * *